(12) United States Patent
Chen

(10) Patent No.: US 7,255,111 B2
(45) Date of Patent: Aug. 14, 2007

(54) DENTAL FLOSS APPLICATOR

(76) Inventor: Cheng-Chuan Chen, 7Fl., No. 25, Lane 121, Hsin Hsing St., Tan Shui Chen, Taipei Hsien (TW)

( * ) Notice: Subject to any disclaimer, the term of this patent is extended or adjusted under 35 U.S.C. 154(b) by 0 days.

(21) Appl. No.: 11/308,624

(22) Filed: Apr. 13, 2006

(65) Prior Publication Data

US 2006/0254610 A1    Nov. 16, 2006

(30) Foreign Application Priority Data

May 10, 2005    (TW) ............................... 94207496 U

(51) Int. Cl.
*A61C 15/00*    (2006.01)
(52) U.S. Cl. ...................... 132/325; 132/323
(58) Field of Classification Search ........ 132/323–329, 132/322

See application file for complete search history.

(56) References Cited

U.S. PATENT DOCUMENTS

| | | | | |
|---|---|---|---|---|
| 3,734,107 A | * | 5/1973 | Thierman | ................. 132/325 |
| 5,269,331 A | * | 12/1993 | Tanriverdi | ................. 132/325 |
| 5,678,578 A | * | 10/1997 | Kossak et al. | ............. 132/322 |
| 7,156,110 B2 | * | 1/2007 | Landry | ....................... 132/325 |

* cited by examiner

*Primary Examiner*—Robyn Doan
(74) *Attorney, Agent, or Firm*—Pai Patent & Trademark Law Firm; Chao-Chang David Pai

(57) ABSTRACT

A dental floss applicator of this invention comprises a housing, a dental floss stick, a floss spool, a spring rack, a take-up wheel, and a rotary knob with a springy ratchet on the inside. The spring rack has a stop portion engaged with a gear wheel fastened to the floss spool to stretch the dental floss, and a press portion extending to the outside of the housing for pressing by the user to loosen the dental floss on the dental floss stick. The springy ratchet releases the stop portion of the spring rack step by step upon rotation of the rotary knob, allowing the used segment of the dental floss to be taken up.

12 Claims, 10 Drawing Sheets

DENTAL FLOSS APPLICATOR

BACKGROUND OF THE INVENTION (a) Field of the Invention

The present invention relates to a dental floss applicator and more particularly to such a dental floss applicator, which automatically synchronously takes up and releases the dental floss and allows adjustment of the tension of the applied dental floss.

(b) Description of the Prior Art

Conventional dental floss sticks are designed for single use only. These disposable dental floss sticks commonly have an F-shaped stick, which has two suspension arms arranged in parallel at one end and a pointed tip disposed at the other end for use as a toothpick, and a piece of dental floss hung between the two suspension arms. Various dental floss bobbins, dental floss dispensers, and dental floss applicators are also commercially available. However, conventional dental floss bobbins and dental floss dispensers have no means to adjust the tension for applying dental floss. When a different material of dental floss is used, the dental floss provides a different tension. It is inconvenient to manipulate a piece of dental floss for cleaning the teeth if the tension for applying piece of dental floss is not properly adjusted.

SUMMARY OF THE INVENTION

The present invention has been accomplished under the circumstances in view. It is one object of the present invention to provide a dental floss applicator, which uses a spring rack with a stop portion to impart a pressure to the dental floss stick, keeping the dental floss stretched. It is another object of the present invention to provide a dental floss applicator, which has a springy ratchet mounted inside a rotary knob to release the spring rack step by step subject to rotation of the rotary knob to take up the used segment of the dental floss. It is still another object of the present invention to provide a dental floss applicator, which has a gear wheel fixedly provided at one side of the floss spool and a conical bolt perpendicularly extending from the center thereof and inserted into a split axle at one cover shell of the housing of the dental floss applicator and secured thereto with a screw, which can be rotated to adjust the stretching force being applied to the dental floss through the spring rack. It is still another object of the present invention to provide a dental floss applicator, which has two insertion holes provided at the front side of the dental floss stick for holding the dental floss, enabling the dental floss to be held on the dental floss stick in a loosed status convenient for fastening to the tooth to be cleaned. It is still another object of the present invention to provide a dental floss applicator, which uses a protective case for selectively capping on the front or rear side of housing to protect the dental floss stick or to use as a handle. It is still another object of the present invention to provide a dental floss applicator, which has a shaft connected to the take-up wheel and fastened to the rotary knob with a screw, and a cutter affixed to the shaft for cutting off the used part of the dental floss after removal of the take-up wheel from the housing.

DETAILED DESCRIPTION OF THE PREFERRED EMBODIMENTS

Figure 1:
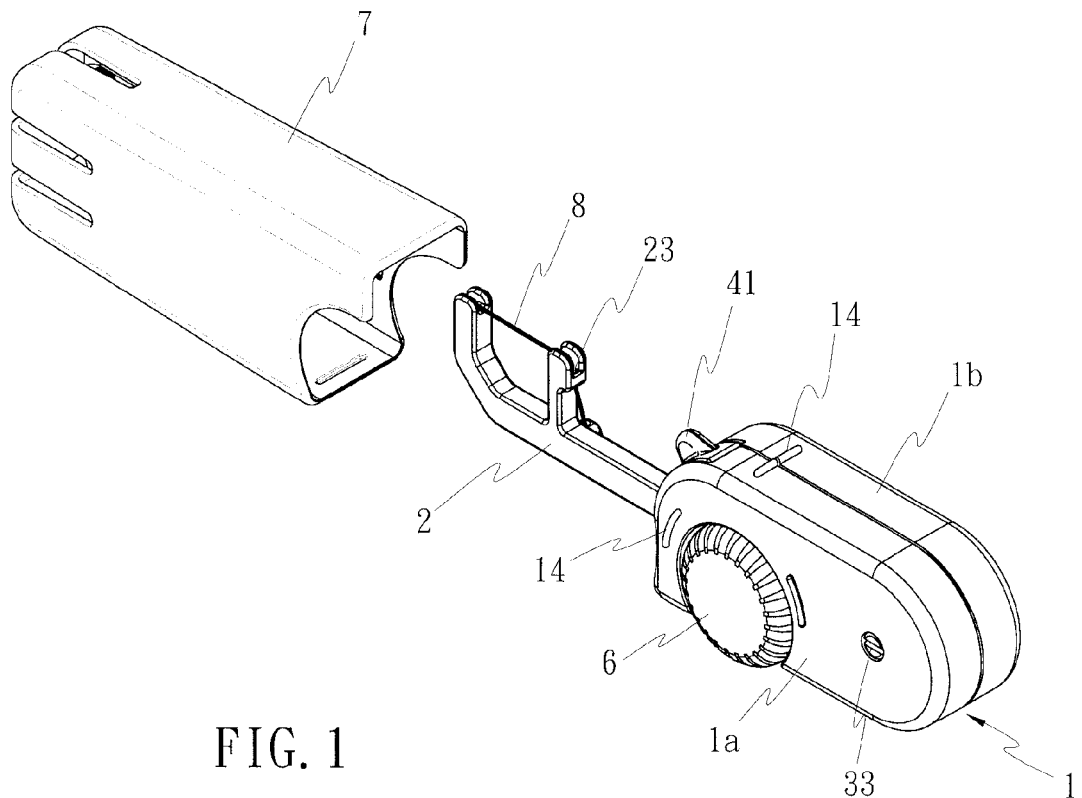
FIG. 1 is a perspective view of a dental floss applicator, showing the protective case removed from the front side of the housing.
Figure 2:
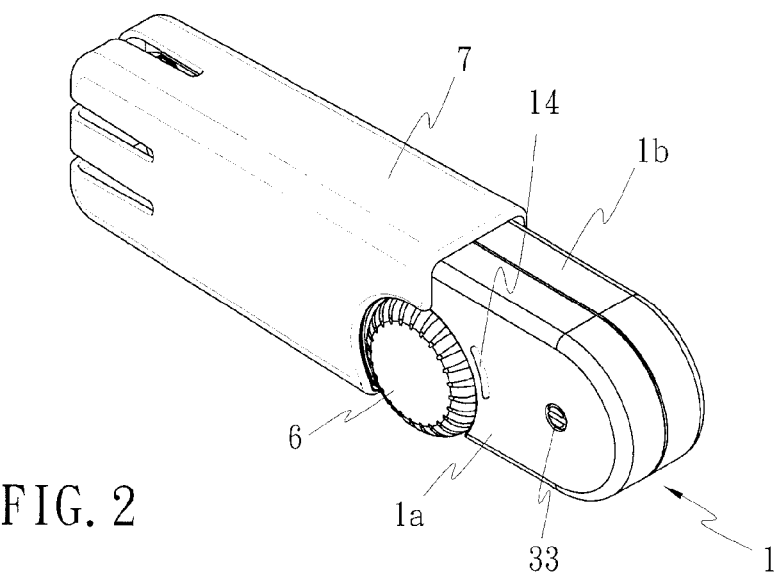
FIG. 2 corresponds to FIG. 1, showing the protective case capped on the front side of the housing.

Referring to FIGS. 1~4, a dental floss applicator in accordance with the present invention is shown comprised of two cover shells 1a and 1b, a dental floss stick 2, a spool 3, a spring rack 4, a take-up wheel 5, and a rotary knob 6.

The two cover shells 1a and 1b are fastened together, forming a housing 1. The housing 1 has a front side adapted to hold the dental floss stick 2. One cover shell 1a has an axle 11a that supports the spool 3, and a through hole 12a. The other cover shell 1b has an axle 11b for supporting a gear wheel 31 and a conical bolt 32 (see FIG. 8), and a recessed chamber 12b corresponding to the through hole 12a.

The dental floss stick 2 can be a F-type or Y-type stick, having a coupling portion 21 at the rear side for coupling to the housing 1, a floss groove 22 and two insertion holes 23 at the front side for the mounting of a predetermined length of dental floss 8 in a stretched condition.

The spool 3 rolls up a certain length of dental floss 8, and is mounted on the axle 11a inside the cover shell 1a. The aforesaid gear wheel 31 is fastened to one side of the spool 3 so that the spool 3 is synchronously rotatable with the gear wheel 31 on the axle 11b. The conical bolt 32 is fitted into the center of the gear wheel 31 and fastened to the axle 11b of the cover shell 1b with a screw 33. The connection between the conical bolt 32 and the screw 33 controls the friction between the axle 11b and the gear wheel 31, thereby controlling the tension of the applied dental floss 8. The dental floss 8 is extended out of the spool 3 through the floss groove 22 of the dental floss stick 2 and then connected to the take-up wheel 5.

Figure 5:
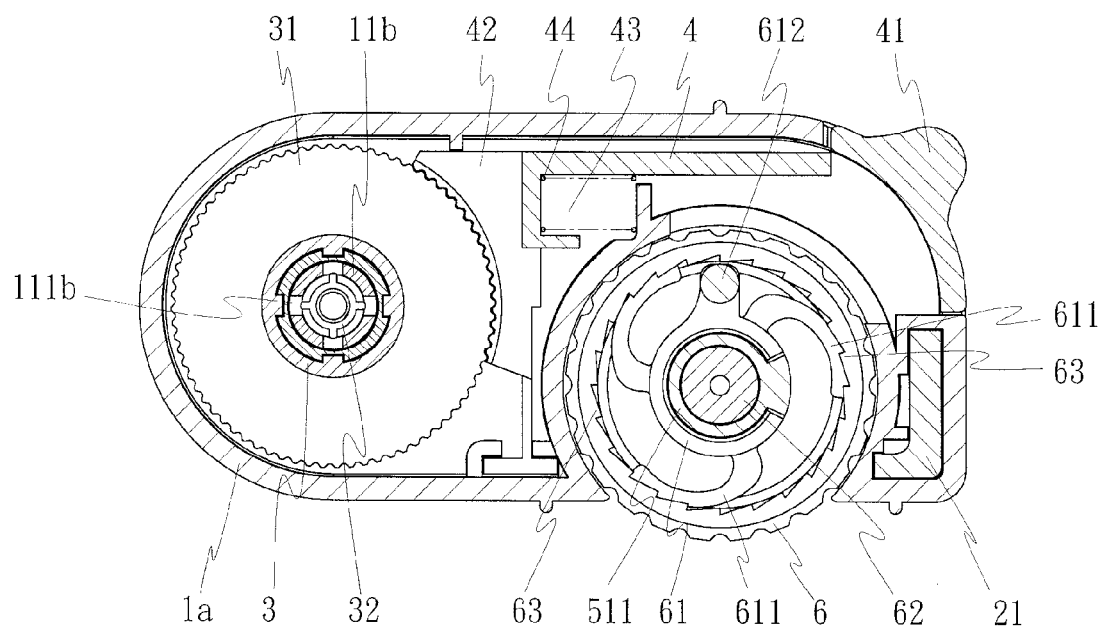
FIG. 5 is a sectional assembly view of the dental floss applicator according to the present invention.
Figure 6:
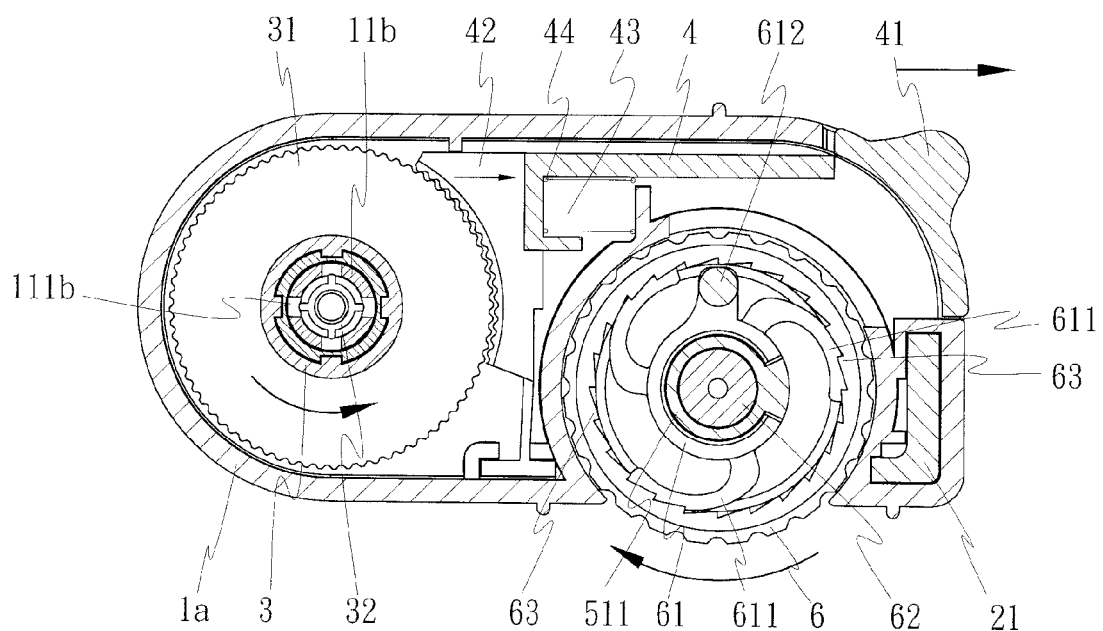
FIG. 6 is a schematic drawing showing the dental floss applicator in operation.
Figure 7:
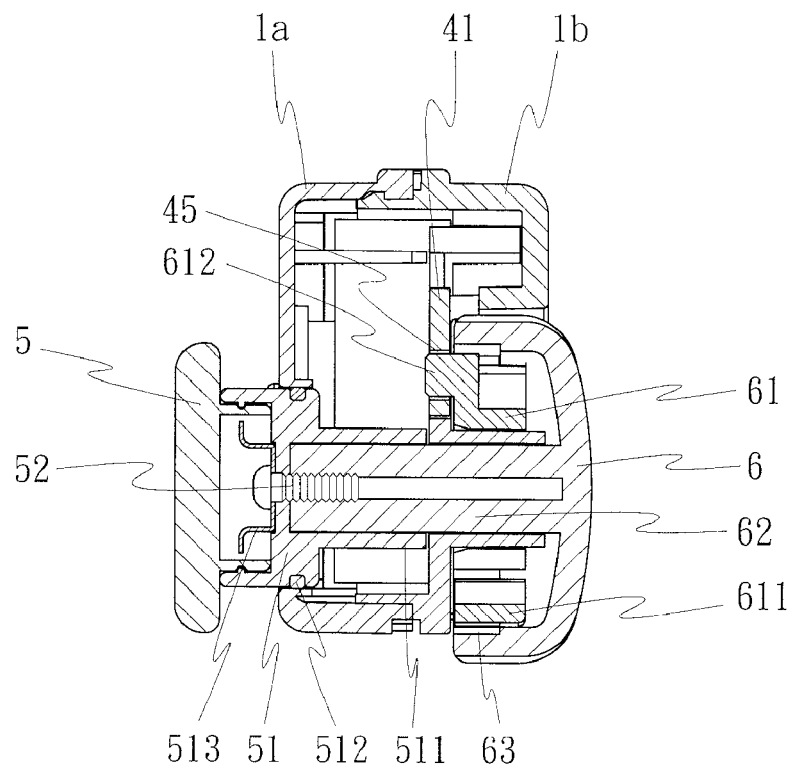
FIG. 7 is a cross sectional view of a part of the present invention, showing the mounting arrangement of the rotary knob.

The spring rack 4 is a substantially L-shaped rack mounted inside the housing 1, having a press portion 41 disposed at one end and suspended outside the housing 1 and a stop portion 42 with a serrated contact face 421 disposed at the other end and engaged with the gear wheel 31 (see FIG. 5). The spring rack 4 further has a receiving chamber 43 for receiving a spring member 44. The spring member 44 has one end stopped against one sidewall of the receiving chamber 43 and the other end stopped against a stop plate 13b at the cover shell 1b. Therefore, the spring member 44 imparts a forward pressure to the spring rack 4, pushing the spring rack 4 toward the outside of the housing 1 for pressing by the user. When the user presses the press portion 41 to push the spring rack 4 backwards, the stop portion 42 is disengaged from the gear wheel 31 for allowing rotation of the gear wheel 31 on the axle 11b (see FIG. 6). The spring rack 4 further has a through hole 45.

The take-up wheel 5 is mounted in the through hole 12a of the cover shell 1a and fastened up with a shaft 51. The other end of the dental floss 8 is fastened to the shaft 51 at the take-up wheel 5. The shaft 51 is mounted with a seal ring 512, having a shaft body 511 fastened to the rotary knob 6 with a screw 52, which also secures a cutter 513 to the shaft 51.

The rotary knob 6 has a shank 62 inserted through a springy ratchet 61 in the recessed chamber 12b of the cover shell 1b and then fastened to the shaft body 511 of the shaft 51 by the aforesaid screw 52, having sloping teeth 63 extending around the inner circumference thereof. The springy ratchet 61 has a plurality of toothed blocks 611 engaged with the sloping teeth 63, and a rod 612 inserted through the through hole 45 of the spring rack 4.

Figure 10:
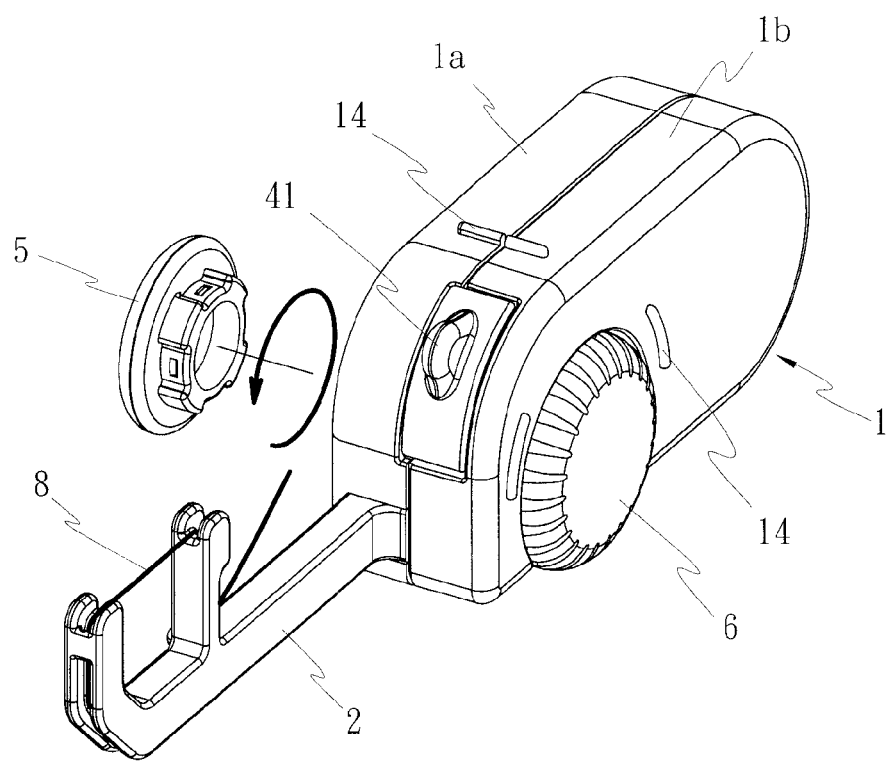
FIG. 10 is a schematic drawing explaining the action of the take-up wheel according to the present invention.

When rotating the rotary knob 6, the take-up wheel 5 and the shaft 51 are rotated, and the springy ratchet 61 is forced to tremble. During trembling of the springy ratchet 61, the stop portion 42 of the spring rack 4 is disengaged from the gear wheel 31 for allowing rotation of the gear wheel 31 on the axle 11b, and therefore the take-up wheel 5 is synchronously rotated with the rotary knob 6 to take up the dental floss 8 from the spool 3 and to wind the used length of the dental floss 8 round the take-up wheel 5 again (see FIG. 10).

Figure 11:
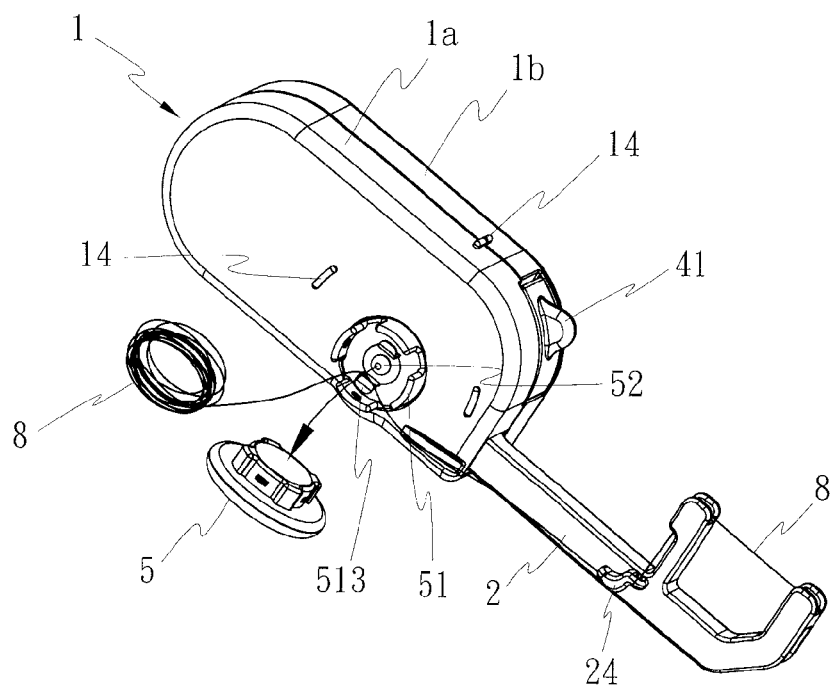
FIG. 11 shows the winding status of the dental floss according to the present invention.

FIG. 11 shows the winding of the dental floss 8. As illustrated, the dental floss 8 extends through the dental floss stick 2 over a guide block 24 to the take-up wheel 5.

Figure 4:
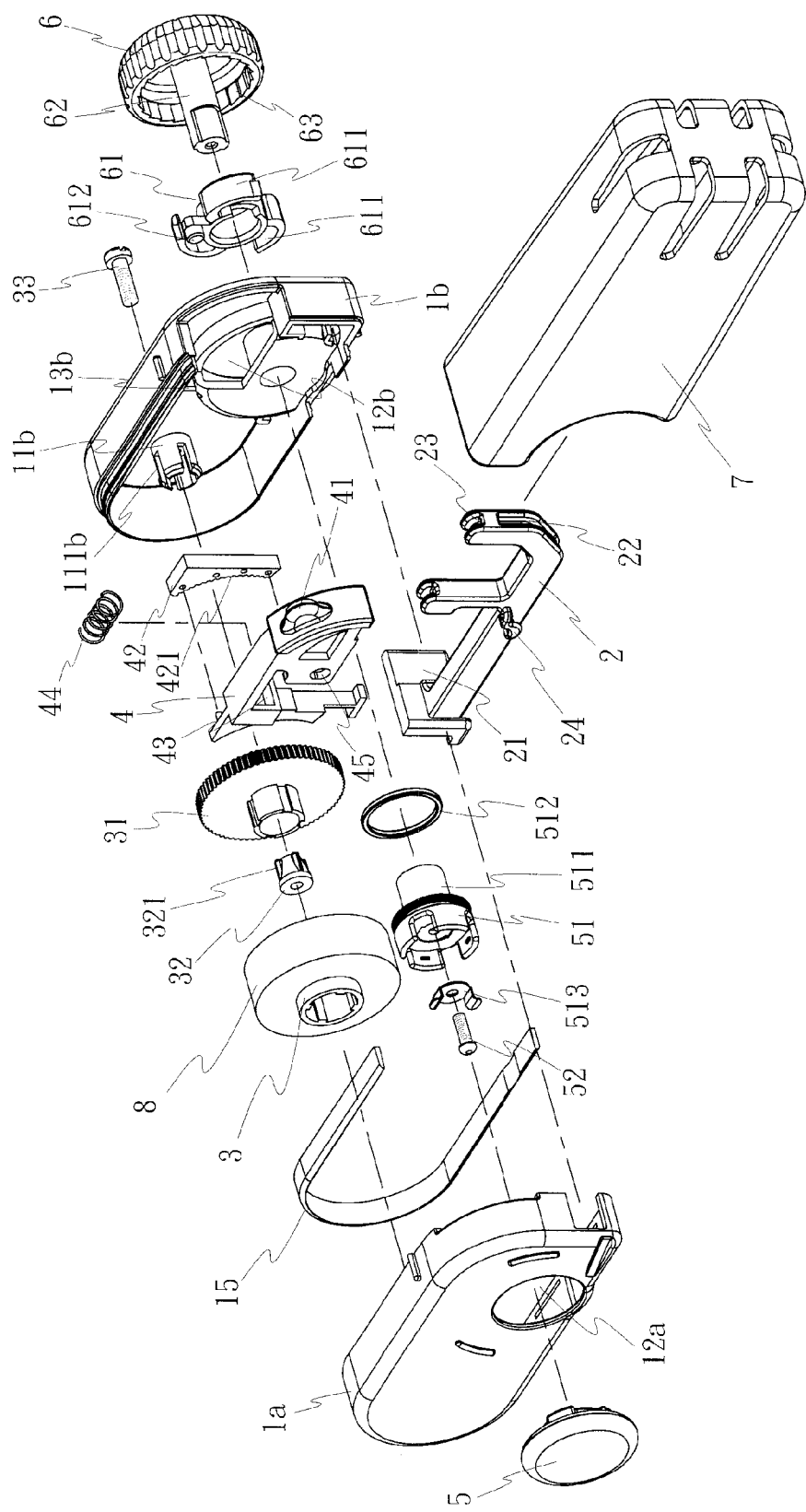
FIG. 4 is another exploded view of the dental floss applicator when viewed from another angle.
Figure 8:
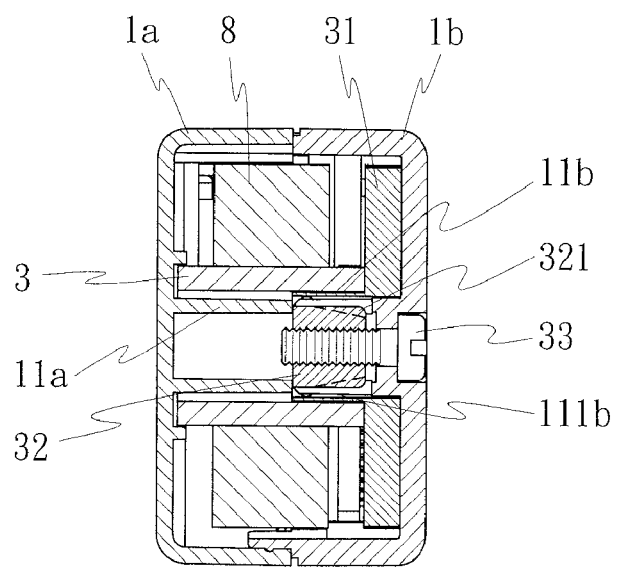
FIG. 8 is a cross sectional view of a part of the present invention, showing the mounting arrangement of the take-up wheel.
Figure 9:
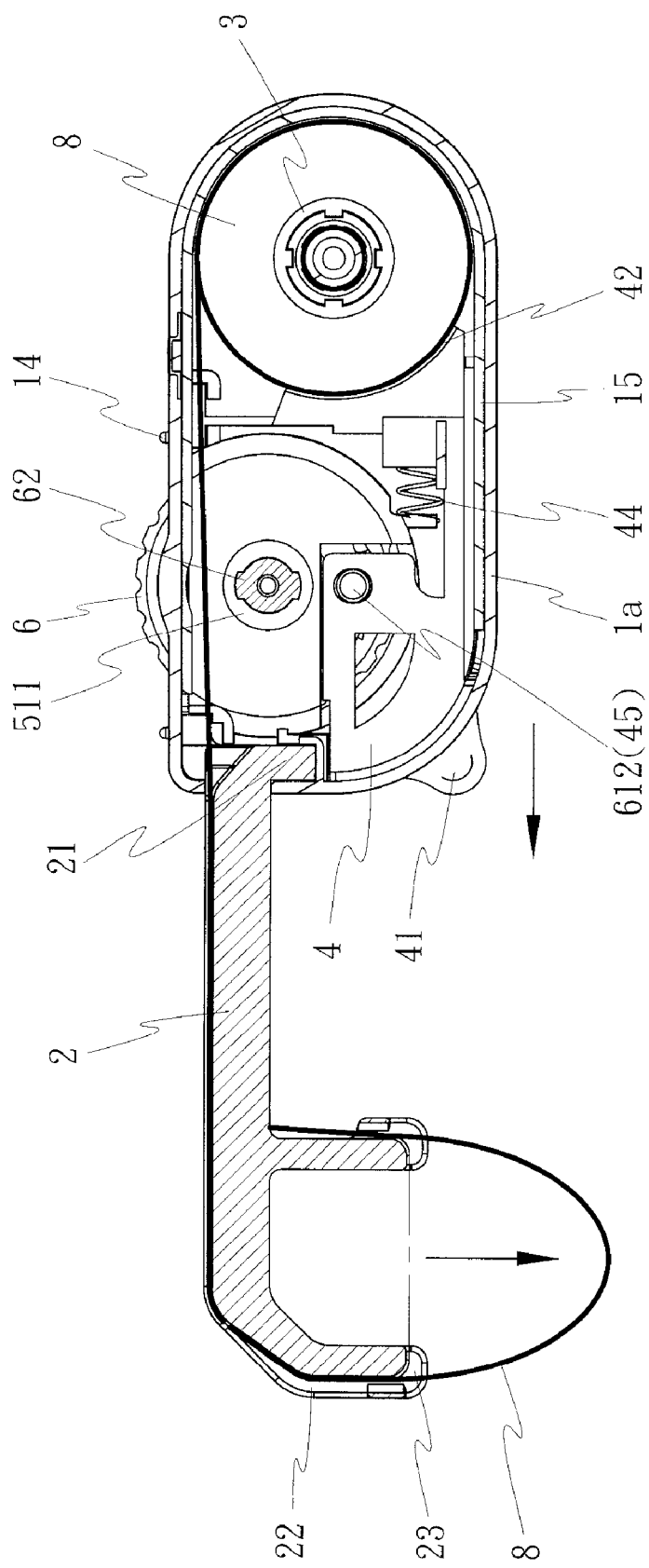
FIG. 9 is a schematic drawing showing the dental floss loosely suspended on the front side of the dental floss stick according to the present invention.

Referring to FIGS. 4 and 8, the conical bolt 32 is mounted on the center of the spool 3 and fastened to the screw 33. The conical bolt 32 has a plurality of radial ribs 321 corresponding to longitudinal crevices 111b on the axle 11b of the cover shell 1b. When fastening the screw 33 relatively tighter, the conical bolt 32 imparts a relatively greater pressure to the axle 11b of the cover shell 1b to stretch the split axle 11b radially outwards, thereby increasing the friction between the axle 11b and the gear wheel 31, and therefore the tension of the dental floss 8 that extends out of the spool 3 is relatively adjusted.

As stated above, the dental floss stick 2 has two insertion holes 23 arranged at the front side for holding a part of the dental floss 8. When the press portion 41 of the spring rack 4 is pressed to disengage the stop portion 42 from the gear wheel 31 for allowing rotation of the gear wheel 31 on the axle 11b, the dental floss 8 is loosely suspended between the insertion holes 23 (see FIG. 8) so that the user can conveniently apply the loosened segment of the dental floss 8 between the two insertion holes 23 of the dental floss stick 2 to the gap between two teeth for cleaning dirt from the gap.

Figure 12:
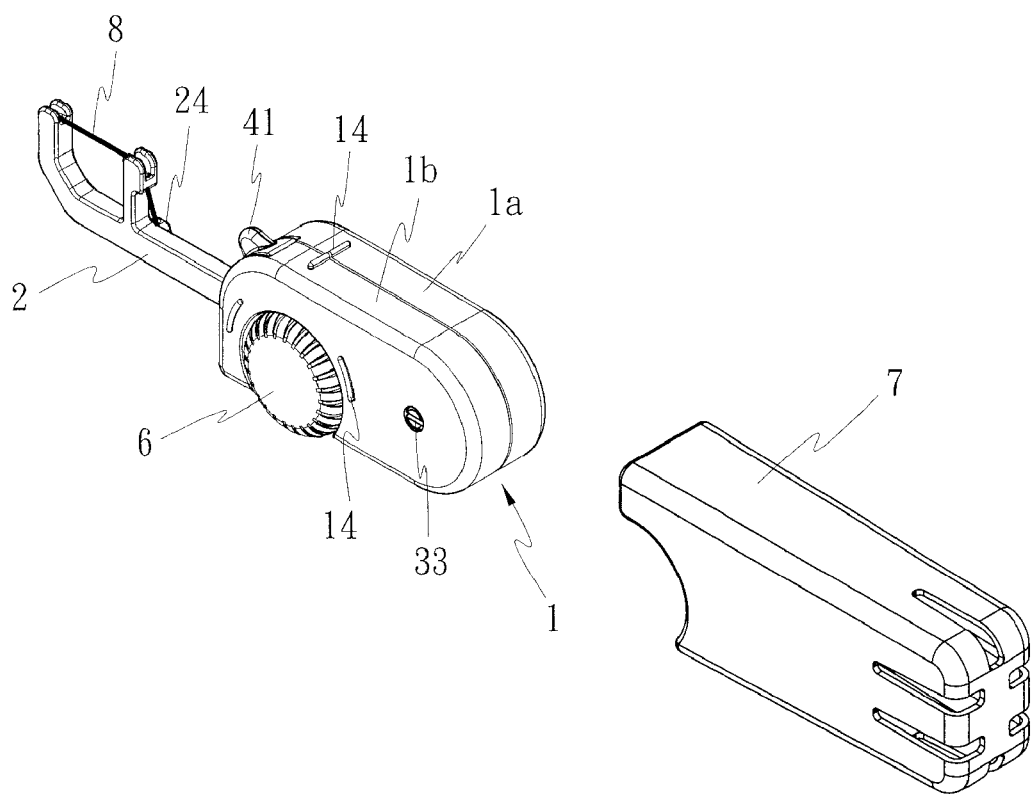
FIG. 12 shows a dental floss applicator with the protective case removed from the rear side of the housing.
Figure 13:
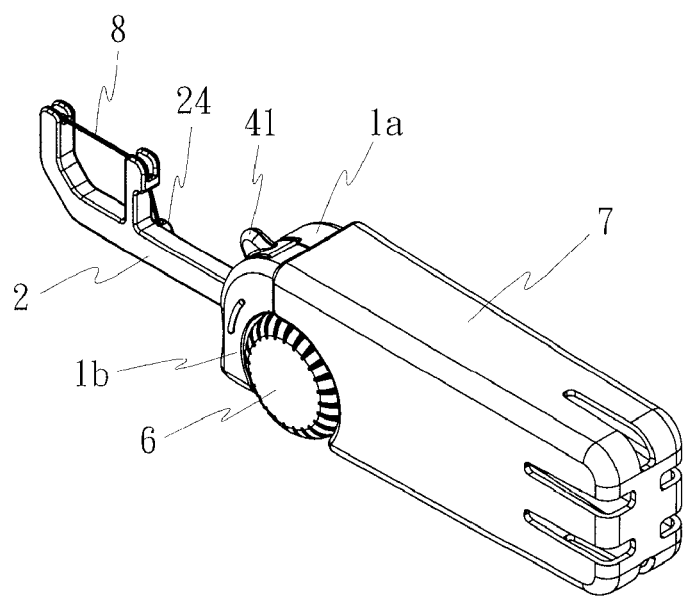
FIG. 13 corresponds to FIG. 12, showing the protective case capped on the rear side of the housing.

Further, a protective case 7 is provided for capping on the front side of the housing 1 to keep the dental floss stick 2 from sight. After removal of the protective case 7 from the front side of the housing 1, the protective case 7 can be capped on the rear side of the housing 1 for use as a handle of the dental floss applicator (see FIGS. 12 and 13). Further, the housing 1 has at least one raised portion 14 that stops against the inside wall of the protective case 7 to secure the protective case 7 firmly in place after the protective case 7 is capped on the housing 1.

Figure 14:
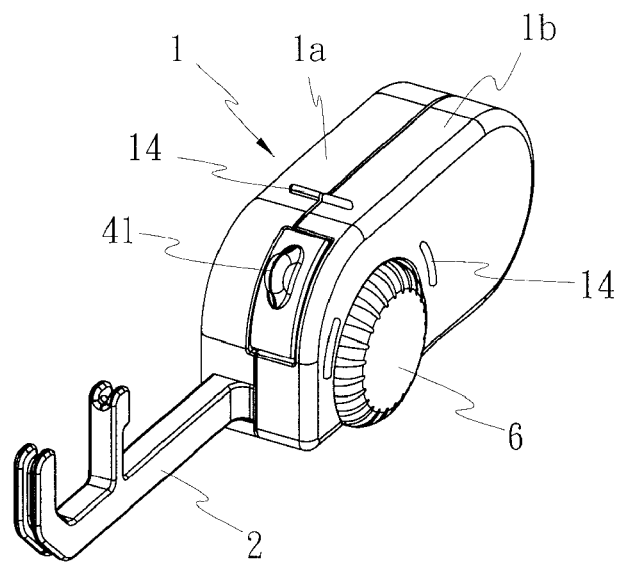
FIG. 14 shows an alternate form of the dental floss applicator according to the present invention.
Figure 15:
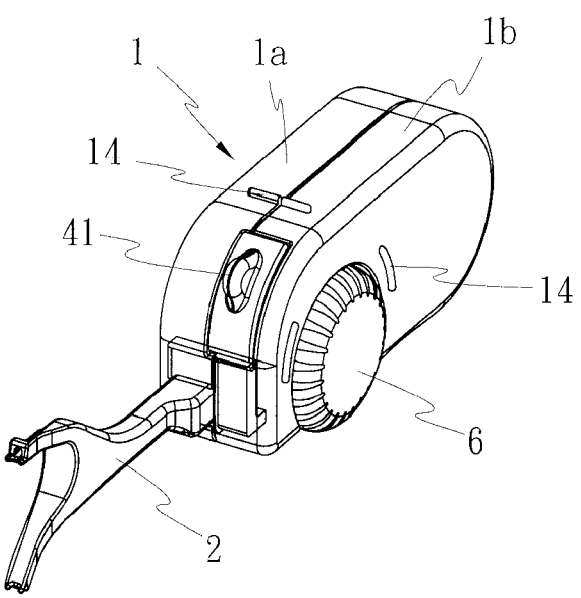
FIG. 15 shows another alternate form of the dental floss applicator according to the present invention.
Figure 16:
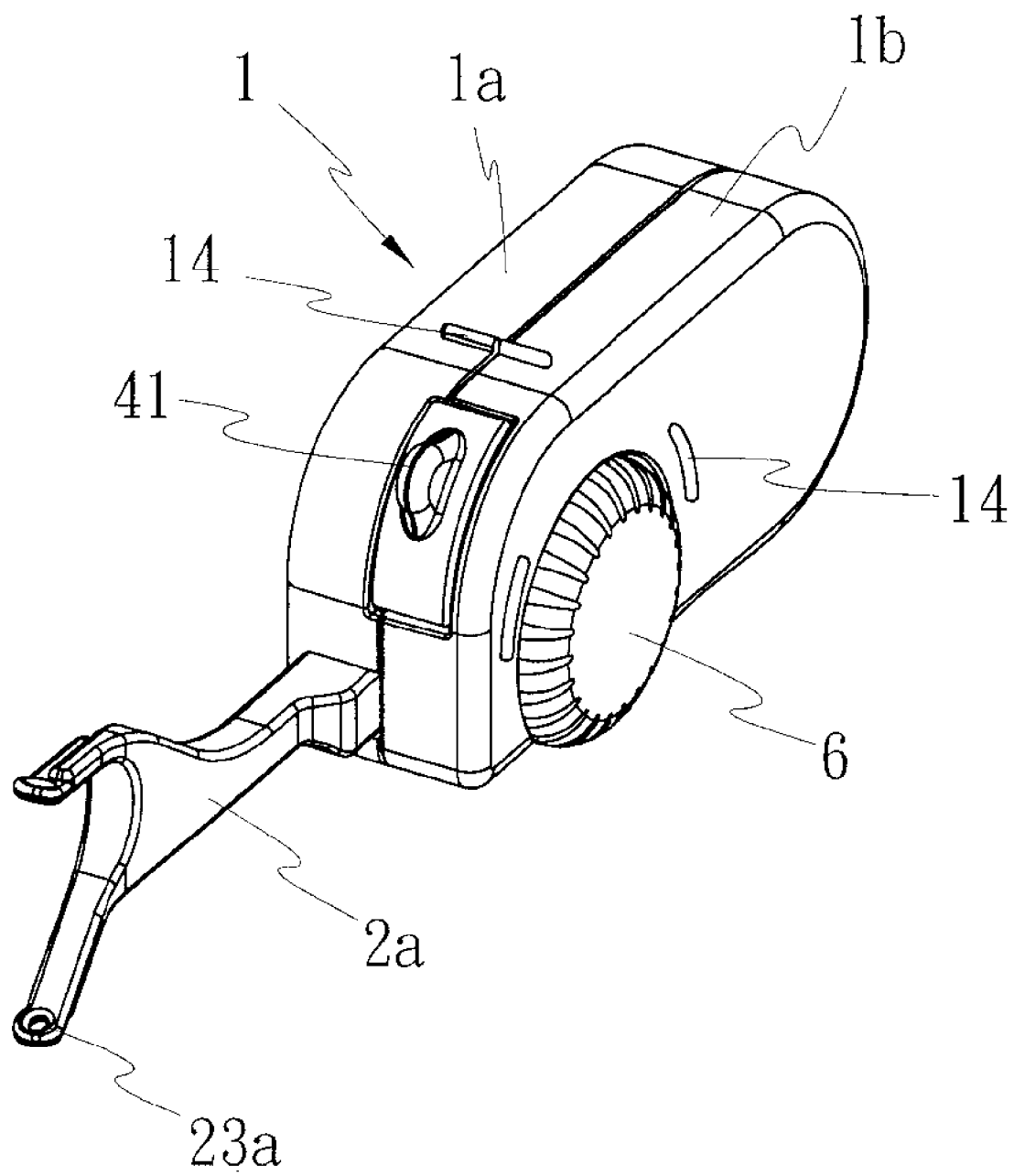
FIG. 16 shows still another alternate form of the dental floss applicator according to the present invention.

FIG. 14 shows an alternate form of the dental floss stick 2. According to this embodiment, the dental floss stick 2 is a F-type dental floss stick without the aforesaid insertion holes 23. FIG. 15 shows another alternate form of the dental floss stick 2. According to this embodiment, the dental floss stick 2 is a Y-type dental floss stick without the aforesaid insertion holes 23. FIG. 16 shows still another alternate form of the dental floss stick 2. According to this embodiment, the dental floss stick 2 is a Y-type dental floss stick with the insertion holes 23.

Figure 3:
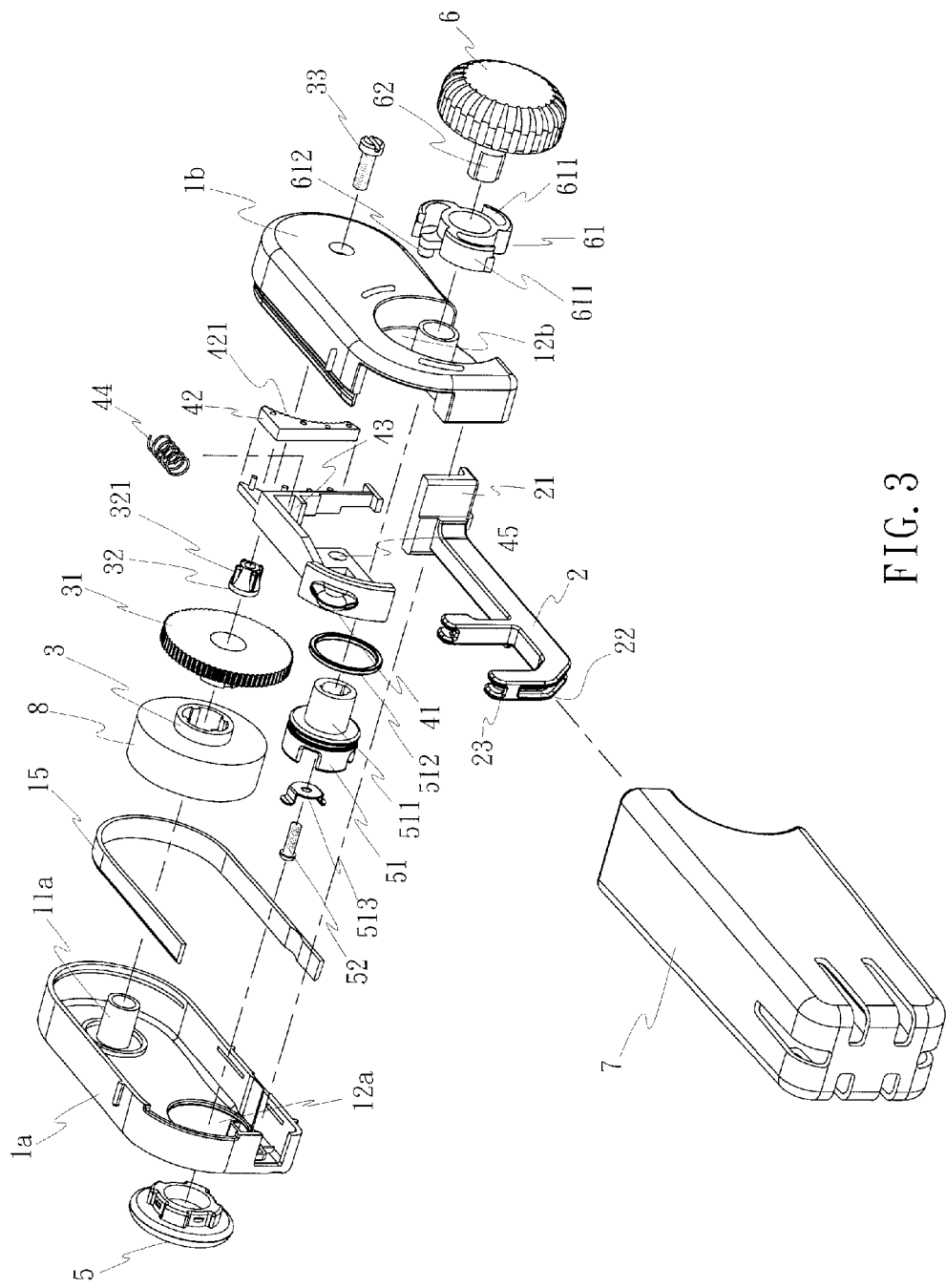
FIG. 3 is an exploded view of the dental floss applicator.

Referring to FIGS. 3 and 4, a rubber packing strip 15 is mounted on the housing 1 to seal the gap between the two cover shells 1a and 1b against water. Therefore, the dental floss applicator can be washed with running water without contaminating the dental floss 8.

Further, the take-up wheel 5 is fastened with the shaft 51 for taking up the used segment of the dental floss 8. After a certain amount of the used part of the dental floss 8 has been received, the user can remove the take-up wheel 5 from the shaft 51 and then use the cutter 513 to cut off the used part of the dental floss 8 (see FIG. 11), and then fasten the take-up wheel 5 to the housing 1 and the shaft 51 again, enabling the end of the dental floss 8 to be jammed in between the take-up wheel 5 and the shaft 51.

A prototype of dental floss applicator has been constructed with the features of FIGS. 1~16. The dental floss applicator functions smoothly to provide all of the features disclosed earlier.

Although particular embodiments of the invention have been described in detail for purposes of illustration, various modifications and enhancements may be made without departing from the spirit and scope of the invention. Accordingly, the invention is not to be limited except as by the appended claims.

What is claimed is:

1. A dental floss applicator comprising:
   a housing formed of two cover shells, said housing having a first axle, a second axle, a through hole, and a recessed chamber;
   a dental floss stick, said dental floss stick having a rear side fastened to a front side of said housing, a front side adapted to support a length of a dental floss in a stretched status, and a floss groove for guiding a dental floss over the front side of said dental floss stick;
   a take-up wheel pivotally mounted in said through hole of said housing and fastened up with a shaft for securing one end of a dental floss and taking up the secured dental floss;
   a floss spool rotatably supported on said first axle, said floss spool having a gear wheel fixedly provided at one side thereof, said floss spool rolling up a dental floss, which has one end extending through the floss groove over the front side of said dental floss stick and connected to said take-up wheel;
   a spring rack mounted inside said housing, said spring rack having a press portion extending out of said housing for pressing by the user, a stop portion suspended inside said housing, said stop portion having a contact face engaged with said gear wheel, a receiving chamber, a spring member mounted in said receiving chamber and stopped between one sidewall of said receiving chamber and a part of said housing, and a through hole;

a rotary knob mounted in said recessed chamber of said housing, said rotary knob having a shank inserted through the through hole of said spring rack and connected to said shaft for rotating said take-up wheel, and a series of sloping teeth extending around and inner circumference thereof; and a springy ratchet mounted on the shank of said rotary knob in said recessed chamber of said housing, said springy ratchet having a plurality of toothed blocks engaged with the sloping teeth of said rotary knob, wherein when said rotary knob is rotated, said take-up wheel and said shaft are rotated, and said springy ratchet is forced to tremble, and said stop portion of said spring rack is disengaged from said gear wheel for allowing rotation of said gear wheel on said second axle during trembling of said springy ratchet, and therefore said take-up wheel is synchronously rotated with said rotary knob to take up the dental floss from said spool and to wind the used length of the dental floss round said take-up wheel again.

2. The dental floss applicator as claimed in claim 1, further comprising a case for covering said housing.

3. The dental floss applicator as claimed in claim 1, further comprising a guide block adapted to guide the dental floss from said dental floss stick toward said take-up wheel.

4. The dental floss applicator as claimed in claim 1, wherein said dental floss stick has two insertion holes provided at the front side thereof for holding a part of the dental floss.

5. The dental floss applicator as claimed in claim 2, wherein said housing has at least one raised portion for providing friction against an inside wall of said case to secure said case to said housing.

6. The dental floss applicator as claimed in claim 1, wherein said dental floss stick is an F-type dental floss stick.

7. The dental floss applicator as claimed in claim 1, wherein said dental floss stick is a Y-type dental floss stick.

8. The dental floss applicator as claimed in claim 1, wherein said second axle is formed of a split tube having at least one longitudinal crevice; said gear wheel has a conical bolt perpendicularly extending from the center thereof and inserted into said split tube of said second axle, said conical bolt having at least one radial rib corresponding to the at least one longitudinal crevice of said split tube of said second axle; and said second axle is mounted with a screw, which is threaded into said conical bolt to secure said gear wheel to said second axle.

9. The dental floss applicator as claimed in claim 1, wherein said spring rack is L-shaped.

10. The dental floss applicator as claimed in claim 1, further comprising a rubber seal ring mounted on said shaft to seal the gap between said take-up wheel and the through hole of said housing.

11. The dental floss applicator as claimed in claim 1, wherein said shaft is fastened to said rotary knob with a screw and a cutter is secured to said shaft.

12. The dental floss applicator as claimed in claim 1, further comprising a rubber packing strip fastened to said housing to seal the gap between said two cover shells against water.

* * * * *